US012201463B2

(12) United States Patent
Jailin et al.

(10) Patent No.: US 12,201,463 B2
(45) Date of Patent: Jan. 21, 2025

(54) METHODS AND SYSTEMS FOR DIGITAL MAMMOGRAPHY IMAGING

(71) Applicant: GE Precision Healthcare LLC, Wauwatosa, WI (US)

(72) Inventors: Clement Jailin, Hauts de Seine (FR); Laurence Vancamberg, Yvelines (FR); Serge Muller, Yvelines (FR); Pablo Milioni De Carvalho, Hauts-de-seine (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 328 days.

(21) Appl. No.: 17/930,313

(22) Filed: Sep. 7, 2022

(65) Prior Publication Data

US 2024/0074718 A1    Mar. 7, 2024

(51) Int. Cl.
*A61B 6/04* (2006.01)
*A61B 6/00* (2024.01)
*A61B 6/46* (2024.01)
*A61B 6/50* (2024.01)

(52) U.S. Cl.
CPC .......... *A61B 6/0492* (2013.01); *A61B 6/461* (2013.01); *A61B 6/488* (2013.01); *A61B 6/502* (2013.01); *A61B 6/5229* (2013.01); *A61B 6/5247* (2013.01); *A61B 6/5258* (2013.01); *A61B 6/5294* (2013.01); *A61B 6/481* (2013.01)

(58) Field of Classification Search
CPC ....... A61B 6/0492; A61B 6/461; A61B 6/502; A61B 6/5247; A61B 6/5258; A61B 6/5294; A61B 6/04; A61B 6/481; A61B 6/463; A61B 6/488; A61B 6/5229
See application file for complete search history.

(56) References Cited

U.S. PATENT DOCUMENTS

| | | | |
|---|---|---|---|
| 8,194,947 B2 | 6/2012 | Zingaretti et al. | |
| 10,593,052 B2 | 3/2020 | Abhari et al. | |
| 10,799,316 B2 | 10/2020 | Sela et al. | |
| 2021/0259649 A1* | 8/2021 | Milioni De Carvalho | ............ G06T 7/337 |
| 2022/0273273 A1 | 9/2022 | Vancamberg et al. | |

FOREIGN PATENT DOCUMENTS

| | | | |
|---|---|---|---|
| DE | 102011080682 A1 | 2/2013 | |
| EP | 3698719 B1 * | 3/2021 | ............ A61B 6/025 |
| WO | 2006055251 A2 | 5/2006 | |

OTHER PUBLICATIONS

DE 102011080682 Translation of Abstract, Espacenet Search Result Jun. 11, 2024; 1 page.
EP application 23192425.9 filed Aug. 21, 2023—Search Report issued Feb. 12, 2024; 8 pages.

* cited by examiner

*Primary Examiner* — David P Porta
*Assistant Examiner* — Casey Bryant
(74) *Attorney, Agent, or Firm* — McCoy Russell LLP

(57) ABSTRACT

Various methods and systems are provided for digital mammography imaging procedures. In one example a method for an x-ray system includes acquiring a comparative image of a patient with an x-ray detector, aligning the comparative image with a reference image which includes an ROI, mapping the ROI of the reference image onto the comparative image. When mapping indicates the ROI is outside of frame of the comparative image, the method includes displaying comparative image with instructions indicating a relative position of the ROI.

20 Claims, 10 Drawing Sheets

METHODS AND SYSTEMS FOR DIGITAL MAMMOGRAPHY IMAGING

FIELD

Embodiments of the subject matter disclosed herein relate to digital mammography imaging procedures.

BACKGROUND

Mammography is a medical imaging procedure for detecting one or more tumors of a breast. Based on mammography imaging in addition to other imaging modalities such as magnetic resonance imaging (MRI), ultrasound (US), and the like, a lesion, or area of abnormal tissue growth, may be identified by a clinician. The identification of a lesion may trigger a request for further treatment such as a biopsy or a contrast enhanced spectral mammography (CESM) exam. In some examples a CESM exam may accompany a biopsy to enhance visualization of the lesion during the biopsy. During a breast biopsy or a CESM-guided biopsy, a scout image (where x-ray tube is in a midline position perpendicular to the detector) may be taken before starting a procedure. The scout image may be used to confirm that the lesion or other area of interest is within a field of view of the procedure. During a breast biopsy, the scout image may additionally be used to confirm that the lesion or other area of interest is within a biopsy volume and therefore accessible to the biopsy practitioner. If the lesion is not viewed in the scout image, a patient may be moved relative to the imaging apparatus and the scout image retaken for confirmation of desired patient positioning before the procedure commences.

BRIEF DESCRIPTION

In one embodiment, a method for an x-ray system includes acquiring a comparative image of a patient with an x-ray detector; aligning the comparative image with a reference image, at a processor, by registering the comparative image to the reference image, the reference image including a region of interest (ROI) corresponding to a lesion; mapping the ROI of the reference image onto the comparative image; and when the ROI is outside of a frame of the comparative image, displaying the comparative image at a display screen with instructions indicating a relative position of the ROI.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
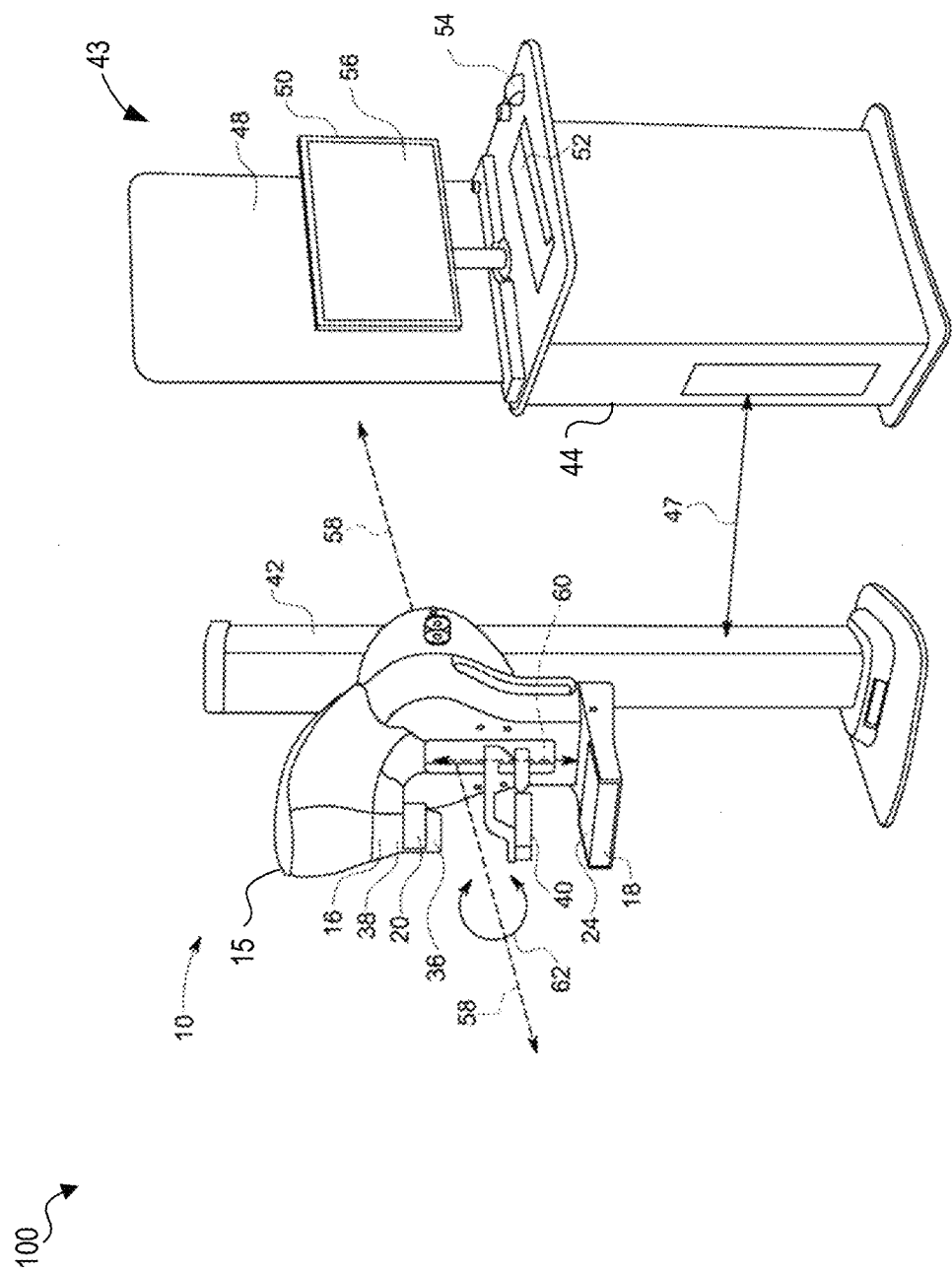
FIG. 1 is an example of a digital mammography system according to an embodiment.

The following description relates to various embodiments for digital mammography imaging procedures. Digital mammography imaging procedures may include acquiring 2-dimensional (2D) or 3D digital images of the breast. During imaging using a digital mammography system, the breast of a patient is compressed and an x-ray source may be rotated around the breast within a range of angles in positive and negative directions from a medial position. In some examples, a lesion may first be identified in the patient by a clinician in a diagnostic digital mammography image or by other imaging modalities such as US or MRI. As a result, the clinician may request a biopsy or additional imaging of the lesion.

Some medical procedures, such as breast biopsies, may be carried out with assistance from contrast-enhanced spectral mammography (CESM) performed with a digital mammography system. CESM includes the administration of a contrast agent, such as iodine, to an imaging subject (e.g., patient). The contrast agent may travel to the patient's vasculature, which may assist in biopsy target (e.g., lesion) visualization. Following administration of the contrast agent, dual energy images may be obtained at various points of the biopsy procedure, such as immediately after contrast agent injection and prior to anesthesia delivery, after anesthesia delivery, after biopsy needle insertion, after firing of the biopsy device, after sample collection, and/or after biopsy clip insertion. A dual energy image may be generated from two images, where the two images include a first image acquired with low radiation energy (termed a low energy image, or LE) and a second image acquired with high radiation energy (termed a high energy image, or HE). A digital subtraction process may be used to generate the dual energy (DE) image from the LE image and the HE image, such that background features are removed from the DE image and the contrast-enhanced features (e.g., the lesion) are more clearly visualized.

In some examples, a scout image may be taken to confirm that a lesion which had been previously identified is within a field of view of the digital mammography system and/or within the desired biopsy volume. If the lesion is not identified in the scout image, the clinician may not be able to determine if the lesion is in the field of view but not easily visible, or if the patient needs to be repositioned relative to the digital mammography system. When a CESM is performed, the scout image may be CESM image and a contrast agent may aid in visualizing the lesion. However, the contrast agent may washout of the lesion and/or other x-ray scattering may occur which may hinder identification of the lesion within the image.

Thus, according to the embodiments disclosed herein, a user or computer aided diagnosis (CAD) program may define a ROI (or pixel position) of the biopsy target in any given reference image. A reference image may be taken via an imaging modality capable of visualizing the lesion such as digital mammography, US, MRI, or the like. The registered lesion position may be highlighted in a subsequent image (e.g., comparative image). The reference image and the comparative image may be acquired by common or different imaging modalities. In one example, the scout image may be the comparative image and the registered lesion position may be indicated in a scout image and a clinician may be informed if the registered lesion position is outside a desired region. In some examples, the clinician may be given instructions for repositioning a patient to bring the registered lesion position within the field of view. Additionally or alternatively, the scout image, an initial CESM image or angulated pair of x-ray images may be used as the reference image.

Figure 2:
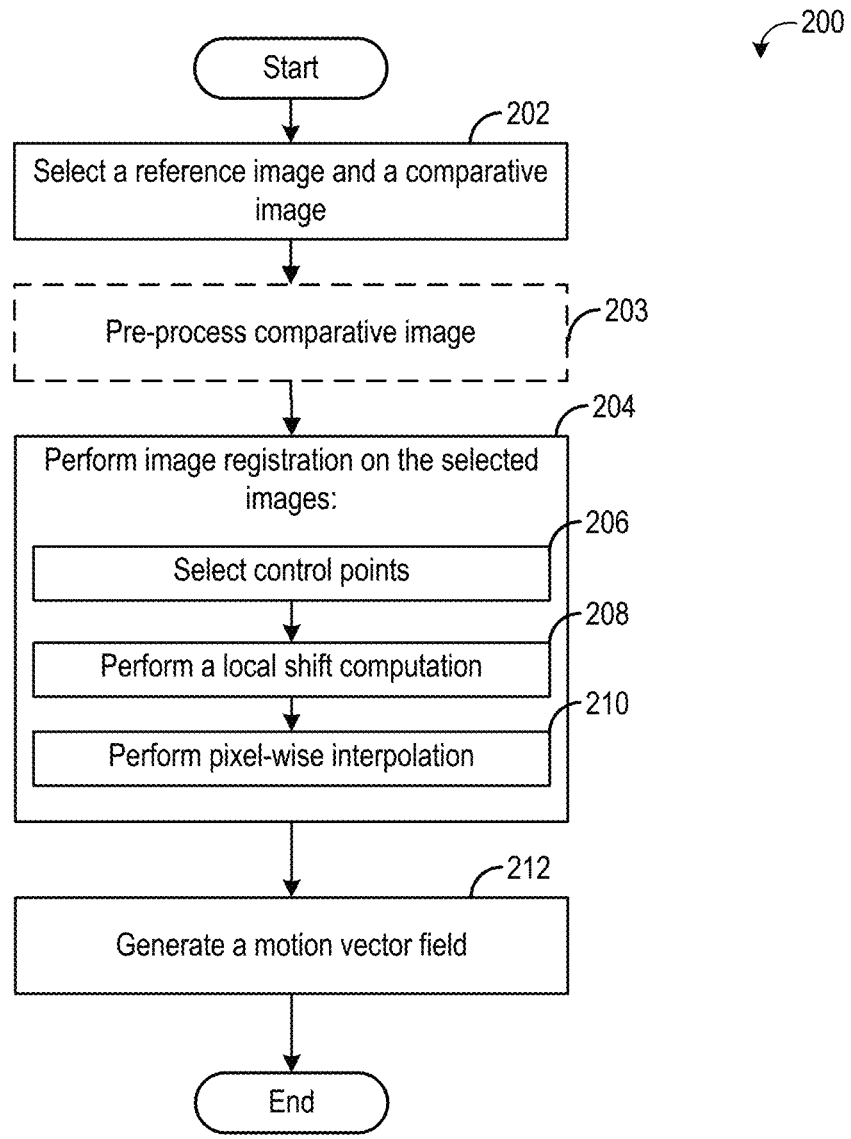
FIG. 2 is an image restoration method according to an embodiment.
Figure 6B:
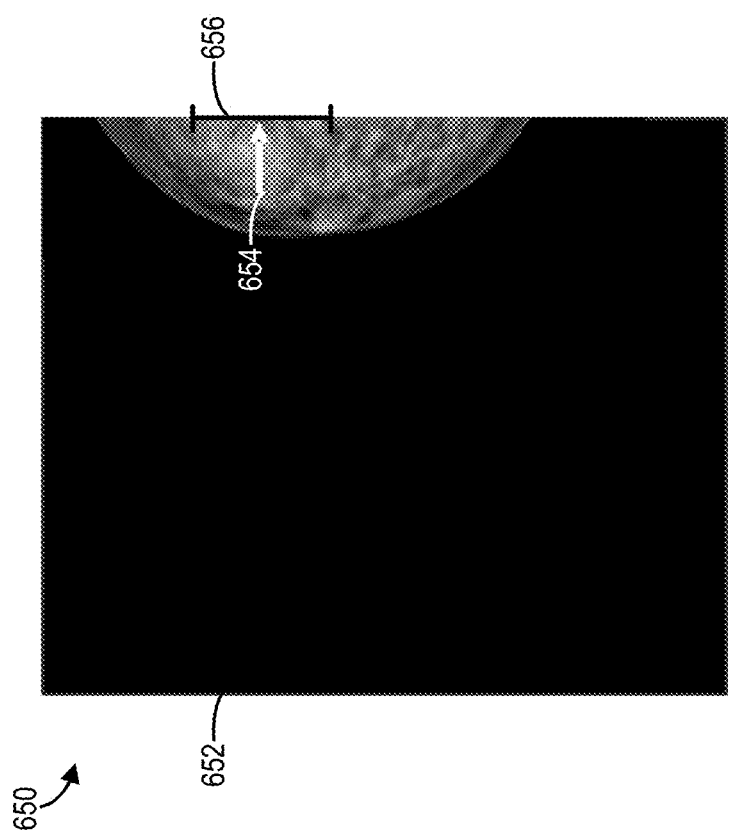
FIGS. 6A-6B show an annotated lesion in and out of an image frame according to an embodiment.
Figure 6A:
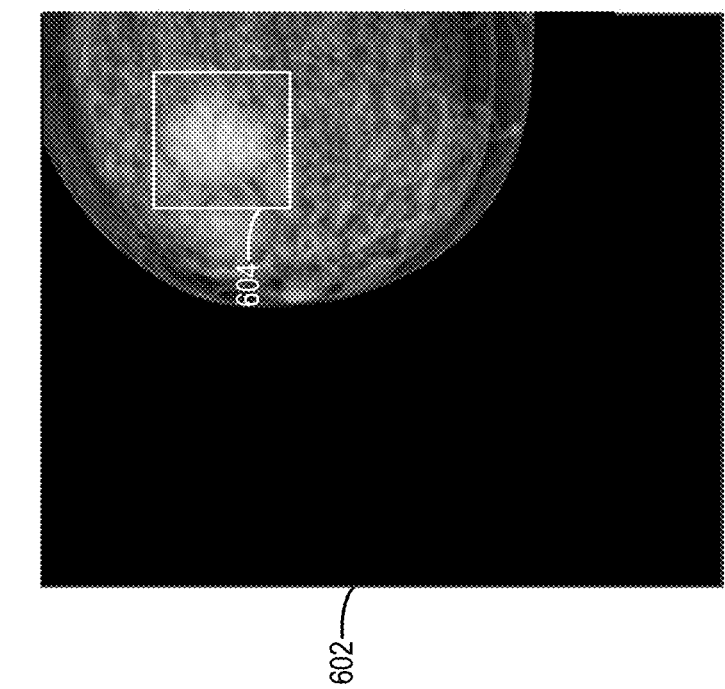
Figure 7:
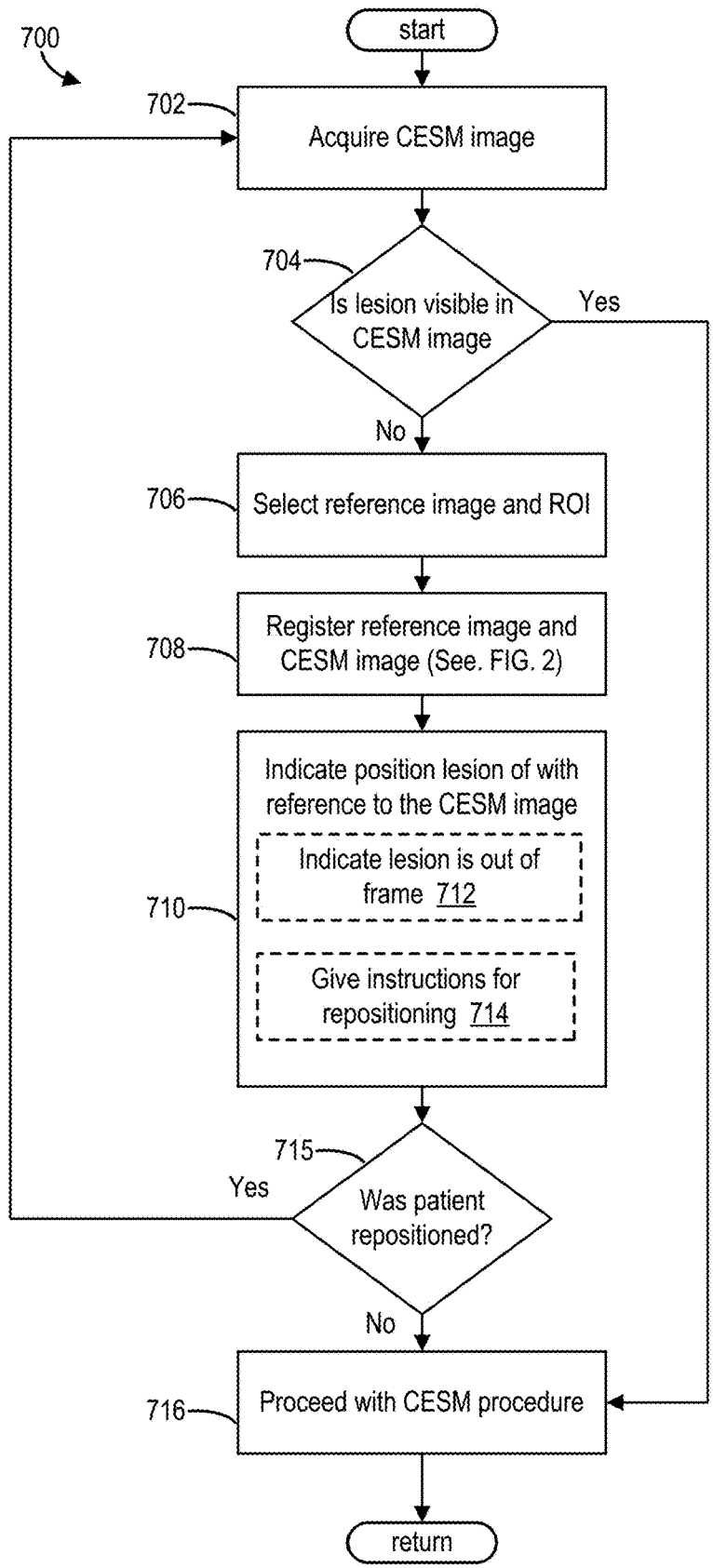
FIG. 7 shows a method for identifying a position of a lesion during a CESM biopsy exam according to an embodiment.

FIG. 1 is an illustration of a digital mammography system which may be used to acquire images, such as CESM images, during a biopsy or other diagnostic procedure. An image registration method, as shown in FIG. 2, may be applied to digital mammography images and/or images from other imaging modalities. The image registration method of FIG. 2 is shown pictorially in FIG. 3. The registered image may be used to locate a lesion in a scout image of a subsequent imaging procedure following a method shown in FIG. 4. The method of FIG. 4 is shown schematically in FIG. 5. A schematic showing an identification of a lesion position both in and out of a field of view is shown in FIGS. 6A-6B, respectively. In another example, a lesion location may be registered in an initial CESM and used to identify the lesion in subsequent CESM images if the lesion location becomes obscured due to washout or scatter. A method for locating the lesion from an initial CESM image registration is shown in FIG. 7. The method of FIG. 7 is shown schematically in FIG. 8. In some examples, CESM images may be acquired as viewed from different angular positions (e.g., angular view pairs) resulting in calculated 3D coordinates. A lesion position may be registered in angular view pairs and used for locating the lesion in subsequent stereotactic images as shown in the method of FIG. 9. The method of FIG. 9 is shown schematically in FIG. 10.

Referring to FIG. 1, a digital mammography system 100 including an x-ray system 10 for performing a mammography procedure is shown, according to an embodiment of the disclosure. The x-ray system 10 may be a used to acquire a scout image and subsequent images for a CESM procedure and/or biopsy procedure.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree in either direction about the axis 58. For example, the angular range of rotation of the radiation source 16 may be $-\theta$ to $+\theta$, where $\theta$ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. The angular range for digital mammography systems may be approximately ±11 degrees to ±60 degrees, depending on the manufacturing specifications.

The radiation source 16 is directed toward a volume or object to be imaged and is configured to emit radiation rays at desired times to acquire one or more images. The radiation detector 18 is configured to receive the radiation rays via a surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of a subject.

In some embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part and hold the body part still in place while optionally providing apertures to allow for insertion of a biopsy needle, such as a core needle or a vacuum assisted core needle. In this way, compression paddle 40 may be utilized to compress the body part to minimize the thickness traversed by the x-rays and to help reduce movement of the body part due to the patient moving. The x-ray system 10 may also include an object support (not shown) on which the body part may be positioned.

The digital mammography system 100 may further include a workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In an embodiment, the communication between the controller and the x-ray system 10 may be via a wireless communication system. In other embodiments, the controller 44 may be in electrical communication with the one or more components of the x-ray system via a cable 47. Further, in an exemplary embodiment, as shown in FIG. 1, the controller 44 is integrated into the workstation 43. In other embodiments, the controller 44 may be integrated into one or more of the various components of the system 10 disclosed above. Further, the controller 44 may include processing circuitry that executes stored program logic and may be any one of different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

The controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part being imaged. The controller 44 may also control how information, including images 42 and data acquired during the operation, is processed, displayed, stored, and manipulated. Various processing steps as described herein with respect to FIGS. 2, 4, 7, and 9 performed by the controller 44, may be provided by a set of instructions stored in non-transitory memory of the controller 44.

Further, as stated above, the radiation detector 18 receives the radiation rays 22 emitted by the radiation source 16. In particular, during imaging with the x-ray system, a projection image of the imaging body part may be obtained at the detector 18. In some embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 50 via a display screen 56.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50. During mammography, the gantry 15 may be adjusted at different angles to obtain images at different orientations, such as a cranio-caudal (CC) image and a medio-lateral oblique (MLO) image. In one example, the gantry 15 may be rotated about the axis 58 while the compression paddle 40 and the detector 18 remain stationary. In other examples, the gantry 15, the compression paddle 40, and the detector 18 may be rotated as a single unit about the axis 58.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from $-\theta$ to $+\theta$, and a plurality of projection images of the compressed breast is obtained at regular angular intervals over the angular range. For example, if the angular range of the x-ray system is $\pm 11$ degrees, 22 projection images may be captured by the detector during an angular sweep of the gantry at approximately one every one degree, generating a set of angulated x-ray images. The plurality of projection images are then processed by the controller 44 to generate a plurality of DBT image slices. The processing may include applying one or more reconstruction algorithms to reconstruct three dimensional image of the breast. Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis.

In some examples, digital mammography system 100 may be configured to perform contrast imaging where contrast agents, such as iodine, can be injected into the patient and travel to the ROI within the breast (e.g., a lesion). The contrast agents are taken up in the blood vessels surrounding a cancerous lesion in the ROI, thereby providing a contrasting image for a period of time with respect to the surrounding tissue, enhancing the ability to locate the lesion.

The use of a contrast agent can be coupled with images of the ROI taken using dual-energy imaging processes and technology. In dual-energy imaging, low-energy (LE) and high-energy (HE) images are taken of the ROI. In particular, contrast enhanced spectral mammography (CESM) (2D) and contrast enhanced digital breast tomosynthesis (CE-DBT) (3D) imaging modalities are performed with dual-energy technology. For each view (single view in CESM, multiple views for CE-DBT), a pair of images is acquired: a low-energy (LE) image and a high-energy (HE) image. In CE-DBT, non-paired HE and LE images may be acquired for each view and an HE volume, LE volume, and recombined CE volumes may be reconstructed for the ROI. For example, the HE and LE views may be interleaved during the CE-DBT scan (alternatively HE, LE, HE, LE, HE, LE, etc.) with a switch from HE to LE then to HE again etc., for each angulated position of the x-ray tube. The LE and HE images are usually obtained at mean energies above and below the k-edge of the contrast agent. At x-ray energies just above the k-edge of the contrast agent, the absorption of x-rays is increased resulting in an increase of contrast from the iodine contrast agent in the HE image.

In dual-energy 3D or stereotactic procedures, LE and HE image acquisitions are performed, with at least two different positions of the x-ray source with respect to the detector. The images are then recombined to display material-specific information with regard to the internal structure of the tissue being imaged. In the case of 3D CESM, for example, after the injection of contrast medium, dual-energy images are acquired at two or more positions of the x-ray tube with respect to the detector. For each of these tube angulations, the low and high-energy images are recombined to produce an image of the contrast medium surface concentration at each pixel to provide an iodine-equivalent or dual-energy (DE) image(s) (for a single view in CESM, and for multiple views for CE-DBT), which in CE-DBT, are used to reconstruct a 3D volume. Image recombination may be performed based on simulations of the x-ray image chain, via calibrations on a reference phantom, or any other suitable 3D-reconstruction process. Additionally, in the continuous mode of acquisition where the x-ray tube moves continuously with interleaved HE and LE images being taken, the LE images are used to reconstruct a LE 3D volume, and the HE images are used to reconstruct a HE 3D volume, with both volumes being recombined in a suitable manner to provide an iodine 3D volume. In some examples, 3D-reconstruction and HE/LE recombination may be performed in a single step.

Before a CESM or a CE-DBT procedure, a scout image may be acquired to confirm that a previously identified lesion is within a desired region of the acquired mage. If a user (e.g., clinician) does not identify the lesion, it may be due to the lesion being outside of the desired region, or the lesion is within the desired region, but obscured for other reasons. For this reason, identification of a position of the lesion in a previous reference image may be used to display a graphical representation of the position of the lesion in the scout image. The reference image may be a previously acquired diagnostic mammogram or image obtained via a different imaging modality such as US or MRI. Additionally, a position of the lesion may become obscured during an imaging procedure, such as a biopsy. In such an example, an earlier image of the imaging procedure may be used as the reference image. In one example, the graphical representation may include indicating that the position of the legion is outside an image frame of the scout image. In this way, the user may confidently confirm the position of the lesion before and/or during a follow-up procedure such as a biopsy.

FIG. 2 is an image registration method 200 that may be applied to images acquired by a digital mammography system (e.g. digital mammography system 100 of FIG. 1) to compare or integrate data obtained within different images from an image set. In some examples, method 200 may compare images obtained with different imaging modalities. As one example, image registration may be used as a preliminary step in other image processing applications, such as to track a lesion in a scout image (see FIG. 4). Method 200 may be executed using computer readable executable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 200 may be executed by another computing device without departing from the scope of this disclosure (e.g., an edge device, a picture archiving and communication system (PACS)).

At 202, method 200 includes selecting a reference image and a comparative image from an image set acquired by the digital mammography system and/or other imaging modalities. In some examples, more than one reference image may be selected. The reference image herein may be defined as the image to which the comparative image (or images) is aligned during image registration. In some examples, the reference image and comparative image may be taken during the same imaging procedure. The reference image may be a low energy image and the comparative image may be a high energy image, in some examples. In other examples (such as when the image registration method is performed to track a CESM biopsy target according to the method of FIG. 7), the reference image may be a low energy image acquired during a point in time when the biopsy target was still visible in contrast-enhanced images and the comparative image may be a low energy image taken at a time subsequent to the reference image, at a point in time when the biopsy target was no longer visible in contrast-enhanced images, and thus motivating the user of the digital mammography system to switch to non-contrast imaging. In still other examples, the reference image may be an image obtained via digital mammography and/or other imaging modalities during a previous imaging procedure and stored in the non-transitory memory of the computing device. The reference image and the comparative image may be images of the same anatomical features/scan plane of the same patient. Further, the reference image and comparative images may be acquired by common or different imaging modalities.

Optionally, at 203, method 200 may include pre-processing the comparative image. In one example, the comparative image may be acquired as part of a biopsy procedure and may therefore include an artifact from a compression paddle used as part of the biopsy procedure (see, for example, artifact 809 of FIG. 8 below). Pre-processing may include defining a relevant region of the comparative image which may be free of artifacts (e.g., between paddle artifacts). As a result of pre-processing, the image registration may ignore the artifacts which may be present in the comparative image and not the reference image.

At 204, method 200 includes performing image registration on the selected images. During image registration, the comparative image may be aligned to the reference image via a spatial domain method. In one example, such as when the reference image and comparative image are of the same imaging modality, the spatial domain method may define features in terms of pixel intensities. In another example, such as when the reference image and comparative image are of different imaging modalities, the spatial domain method may define features in terms of geometrical location and/or morphologic characteristics. The spatial domain method may include selecting control points within the reference image and the comparative image at 206. The control points may be individual pixels or groups of neighboring pixels. The control points may be selected randomly in one example. In another example, the control points may be selected based on a predefined grid or other pattern. In a still further example, the control points may be selected based on which pixels/anatomical regions of the comparative image are likely to move from image to image, such as pixels at edges of anatomical structures. The control points may be at the same location in each of the reference image and the comparative image.

At 208, a local shift computation may be performed between the control points of the two images. The local shift computation may indicate, for each control point of the comparative image, the magnitude and direction of shift of that control point relative to the reference image. For example, the local shift computation may generate a motion vector that comprises the vector difference between the position x,y (for rows and columns) of the same clinical/anatomical feature (e.g., a micro calcification or a lesion) in the two images: dx=x1−x2, dy=y1−y2.

At 210, pixel-wise interpolation may be performed based on the local shift computation. The interpolation may include a first interpolation that is performed to pass from the motion vectors at each control point to a motion vector field with motion vectors at every image pixel (e.g., the pixel wise interpolation 309 in FIG. 3). The first interpolation may include B-spline interpolation or another suitable interpolation. Thus, the first interpolation may include a B-spline interpolation to generate a motion vector field, as indicated at 212, where the motion vector field includes a respective motion vector at every pixel based on the motion vectors at the control points. A second interpolation may be performed where, for every pixel p (xp, yp) in the comparative image (e.g., the image that is being registered), the vector field value at pixel p (dx,dy) is used to retrieve the image pixel value in position (xp+dx, yp+dy) in the same image (because that is where the pixel is supposed to be, according to the reference image). Since dx and dy are not integer values, interpolation is performed on the surrounding pixels using a linear or cubic function, for example, which may create a registered image as explained below.

Figure 3:
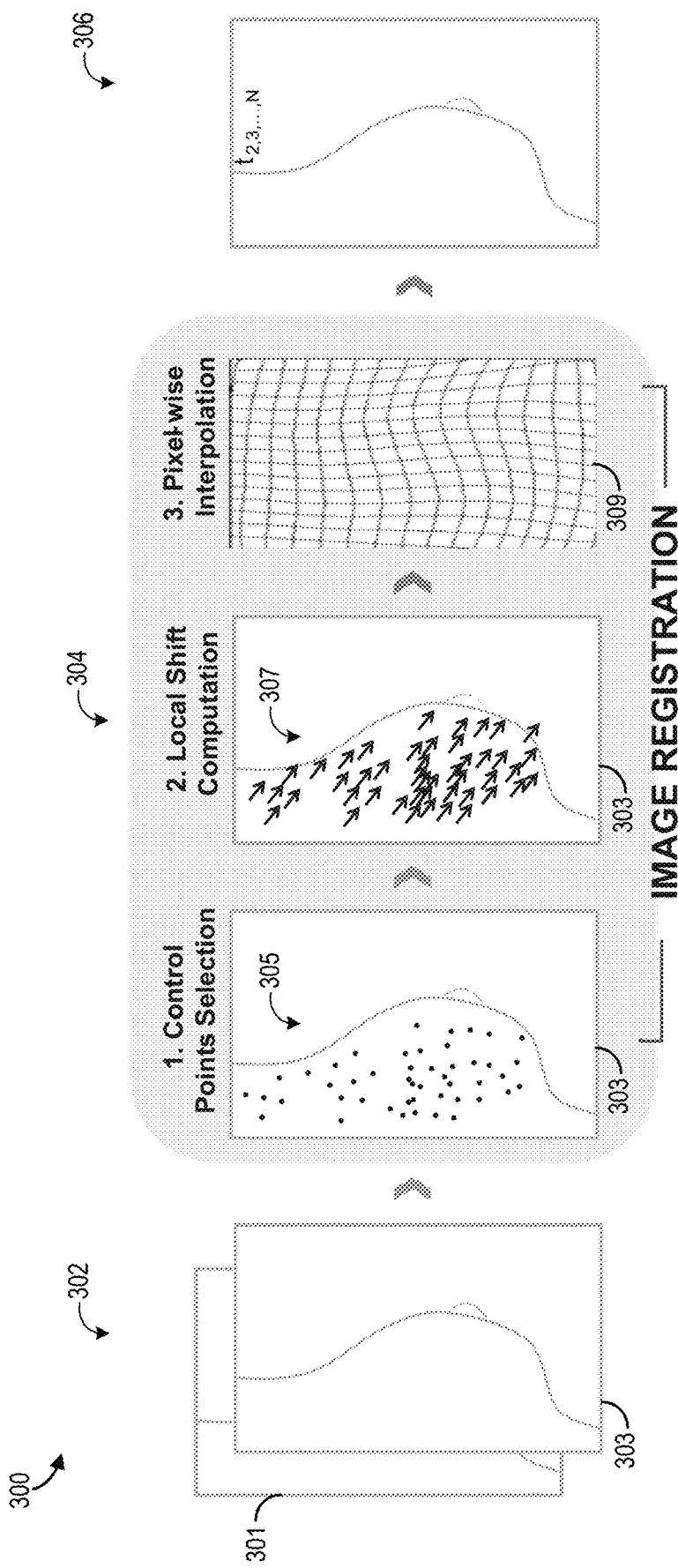
FIG. 3 shows a process for image registration according to an embodiment.
Figure 4:
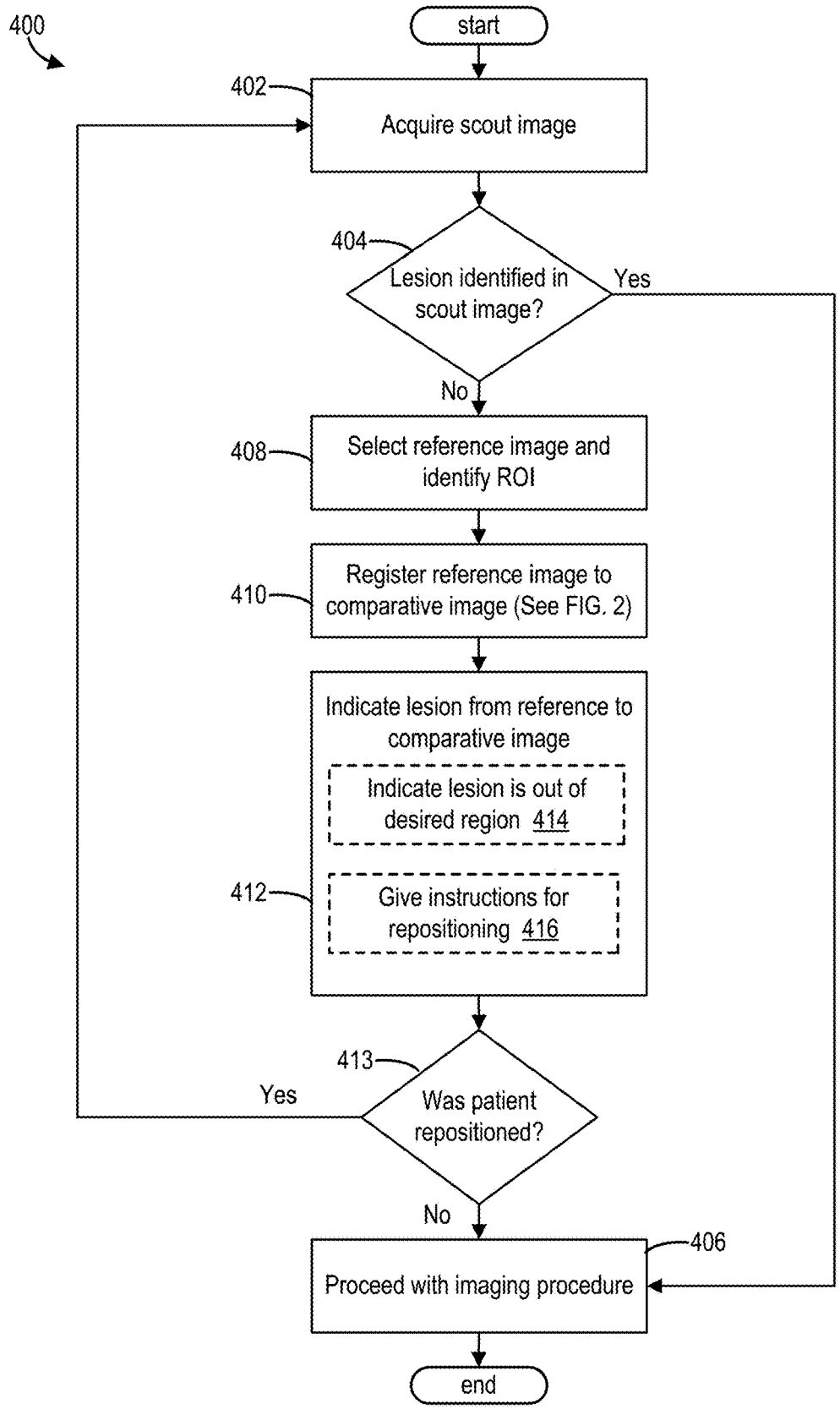
FIG. 4 is a flow chart of a method for identifying a position of a lesion in a scout image according to an embodiment.

FIG. 3 shows an example image registration process 300 according to an embodiment of the disclosure. The image registration process 300 shown in FIG. 3 may be carried out according to the method of FIG. 2. The image registration process 300 includes the registration of two images, shown at 302. The two images include a reference image 301 and a comparative image 303. The reference image 301 may be acquired at an earlier point in time or with a different imaging modality than the comparative image 303. As explained above, the reference image may be a reference LE image acquired during peak contrast enhancement (or least when a biopsy target is sufficiently visible) while the comparative image may be an LE image acquired at any point after the reference LE image. In another example, the reference image 301 may be a previously obtained image acquired via digital mammography, ultrasound, MRI, or similar imaging modalities.

At 304, the two images are registered by selecting control points, computing a local shift at each control point, and performing a pixel-wise interpolation. Example control points 305 and example local shift vectors 307 are shown on comparative image 303. As appreciated by FIG. 3, the local shift computation may include determination of a vector quantifying direction and magnitude of motion/shift for each control point of the comparative image relative to the corresponding control point of the reference image. The pixels of the comparative image are then interpolated on a pixel-wise basis using an interpolation grid 309. Each pixel may be interpolated based on the pixel values of neighboring pixels and the motion vectors as described above. The output of the image registration process 300 is a registered image 306, which may in some examples be the comparative image 303 with adjustments made to some pixels in order to register (e.g., align) features of the comparative image 303 with the reference image 301. However, when tracking a biopsy target with a target marker, the output of the image registration process may include an indication of where, in the comparative image, the lesion target is located, based on determining movement of pixels/tissue in the comparative image relative to the reference image. In one example, the output of the image registration process may include an indication that the lesion target is out of the field of view. Further, in some examples, the output of the image registration process may include instructions to the user for re-positioning in order to position the lesion within the field of view.

Turning now to FIG. 4, a method 400 is shown for using an image registration process (such a method 200 of FIG. 2) to determine a position of a lesion relative to a desired region of a scout image acquired by a digital mammography system. Method 400 may be executed using computer readable executable instructions stored in the non-transitory memory of a computing device of a digital mammography system (e.g., digital mammography system 100 of FIG. 1) or a controller communicatively coupled to the digital mammography system (e.g., controller 44 of FIG. 1). Outputs of method 400 may be visualized on a display connected in communication with the computing device. In some embodiments, method 400 may be executed by another computing device without departing from the scope of this disclosure (e.g., an edge device, a picture archiving and communication system (PACS)).

At 402, method 400 includes acquiring a scout image. The scout image may be obtained with the x-ray source in a single/fixed position (e.g., a medial position, obtained with the x-ray tube positioned at zero degrees from a midline axis perpendicular to the top surface of the detector). The scout image may be a low dose, short exposure image. In some examples, a brightness of the scout image may be assessed to determine the x-ray technique (e.g., x-ray source current and voltage) for subsequent images.

At 404, method 400 includes determining if a lesion is identified in the scout image. Identifying the lesion may include both confirming the lesion is seen in the scout image and that it is the same lesion that was identified in a prior diagnostic image. The lesion may be identified by either a user (e.g., technician) or CAD instructions also included in the controller. If the lesion is identified, method 400 proceeds to 406 and includes proceeding with an imaging procedure. The imaging procedure may be a biopsy performed with CESM or CE-DBT. If the lesion is not identified in the scout image at 404, method 400 proceeds to 408. The lesion may be considered not identified if the user does not see the lesion in the scout image or if the user sees a feature, but is unsure if it is the previously identified lesion.

At 408, method 400 includes selecting a reference image and identifying a ROI. In some examples, one or more reference images may be selected. The reference image may be an image acquired during a separate imaging procedure performed previously where the lesion has been identified by either a user or CAD. The reference image or images may be common or different imaging modality than the scout image. In one example the reference image may be a previous digital mammography image. In other examples, the reference image may be pervious ultrasound or MRI image. In an example where the user sees a feature, but is unsure if it is a lesion, the scout image may be the reference image. A first ROI indicating a location of the lesion on the reference image may be placed on the reference image by the user or by a CAD to identify the first ROI.

At 410, method 400 includes registering the reference image selected at 408 to a comparative image. As one example, the comparative image may be the scout image acquired at 402. In an example where the scout image is the reference image, an image acquired previously where the lesion was identified may be a comparative image to which the scout reference image is registered. Image registration may include mapping of features of the reference image onto a comparative image (e.g., the scout image) as described above with respect to FIGS. 2-3. Features may be intensity and/or geometry based.

At 412, method 400 includes reporting a position of the lesion from the reference image to the comparative image. The position may be reported by a second ROI generated on the comparative image. In one example, a position of the lesion may be shown on the scout image as a result of registering the scout image to the reference image at 410. In an example where the scout image is the reference image, the second ROI may be generated on the previous image. In this way, the second ROI may allow the user to confirm if the lesion identified in the scout image is the same as the lesion identified in the previous image.

If second ROI generated at 412 indicates that the lesion is not positioned in a desired region, at 414, method 400 may include providing an indication that the lesion is out of the desired region. The indication may be a first notification which is written or symbolic (e.g., arrows or brackets) instructions. In some examples, the first indication may be an audio notification. In some examples, method 400 may also include, at 416, providing repositioning instructions (e.g., move patient to the left) to help position the lesion within the scout image for a subsequent image. Further, the second ROI may be used for comparing a position of the lesion to a biopsy volume, including repositioning instructions which may help position the lesion within the biopsy volume for a biopsy procedure. The desired biopsy volume may be indicated on the scout image by a second notification including a square indicating the biopsy volume generated at a display of the computing device (e.g., workstation). First or second notifications may include written or symbolic repositioning instructions. Repositioning instructions may be displayed written text instructions on a screen of a display device of the digital mammography system (e.g. workstation 43 of FIG. 1). Additionally or alternatively, repositioning instructions may be displayed symbolically as arrows on the screen of the display device indicating a direction to move the patient. In some embodiments, repositioning instructions may be given by an audio notification. An embodiment illustrating indication of the first ROI and the second ROI is shown in FIG. 5.

At 413, method 400 includes determining if the patient was repositioned. The patient may be repositioned following step 412 if the identified position of the lesion is outside a desired biopsy volume or outside a desired region of the scout image. If the patient was repositioned, method 400 returns to 402 and the scout image is re-acquired. If the patient was not repositioned, method 400 proceeds to 406. The patient may not be repositioned after step 412 if after the lesion position is identified, it can be seen that the patient was positioned properly, but the lesion was not visible due to other reasons, such as obscuring of the lesion by a biopsy needle or contrast agent washout.

In this way, the user may know a position of the lesion with greater certainty and, if required, may reposition the patient to successfully view the lesion in a subsequent scout image. The procedure may therefore be shorter than repositioning of the patient by the user via trial-by-error, e.g., without guidance. Further, the method may allow distinction between whether the lesion is not visible due to position or if the position is correct but the lesion is not visible due to other reasons (e.g., scatter or washout). Additionally, a number of scout image retakes may be reduced thereby reducing the patient's x-ray dosage.

Figure 5:
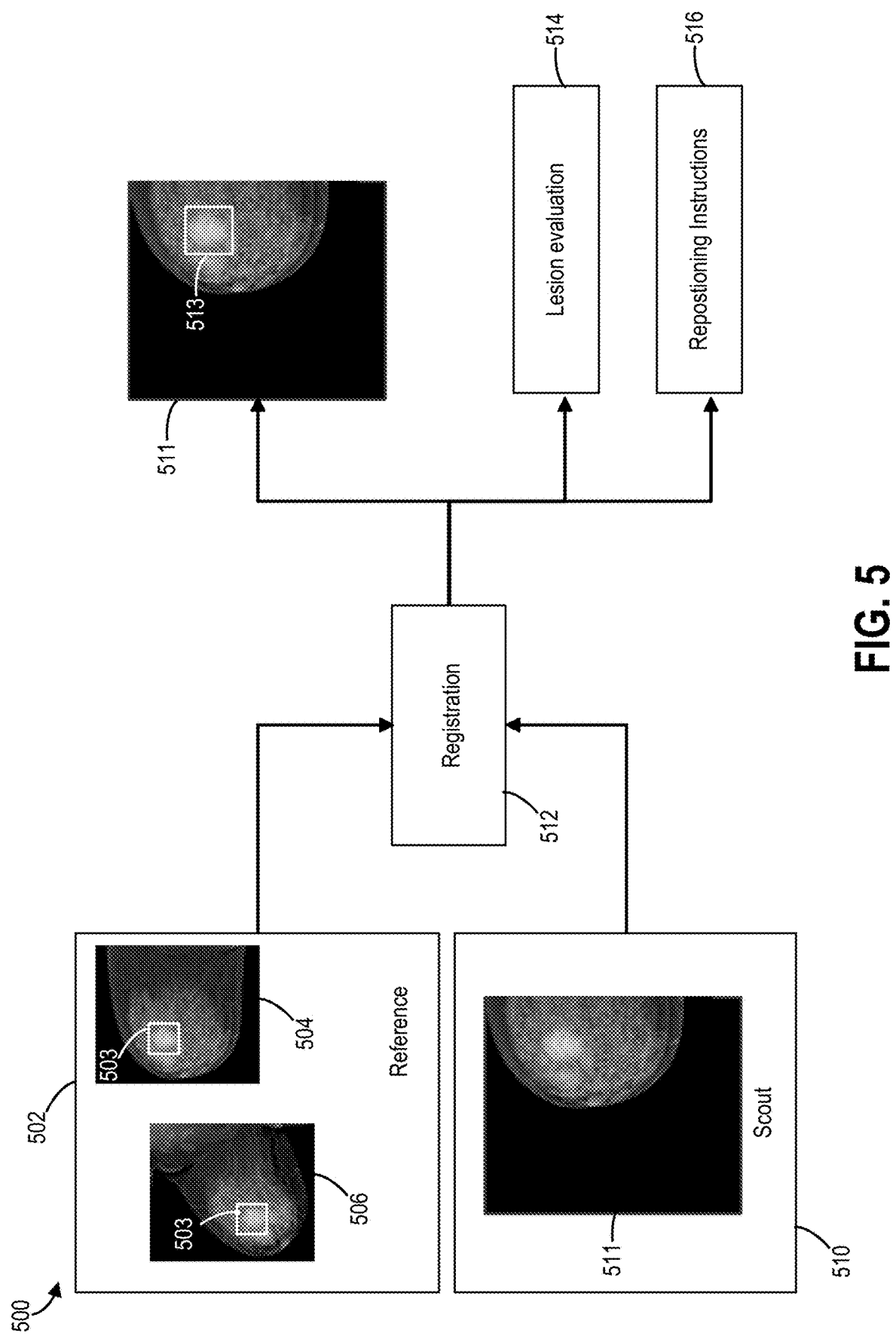
FIG. 5 schematically shows a process for identifying a position of a lesion in a scout image according to an embodiment.

Method 400 may be shown schematically via diagram 500 of FIG. 5. Diagram 500 may include reference images 502 and comparative image 510. In one example, as shown in FIG. 5, comparative image 510 may include a scout image 511 acquired at a start of an imaging procedure. A lesion may or may not be in the field of view of scout image 511. Reference images 502 may include a first view of the lesion 504, and a second alternate view of the lesion 506. Reference images 502 may be taken during a separate imaging procedure performed before acquiring scout image 511. In some examples, reference images 502 may be acquired using a different imaging modality than the imaging modality by which scout image 511 was acquired. Each reference image 502 may include a first ROI 503 indicating a position of the lesion within the image. The first ROI 503 may be placed by a user or by a CAD program.

Comparative image 510 and reference images 502 may be inputs of registration process 512. Registration process 512 may include overlaying features of comparative image 510 and reference images 502 as described above with respect to FIGS. 2 and 3. One or all of reference images 502 may be inputs of registration process 512.

Outputs of registration process 512 may include scout image 511 annotated with a second ROI 513. The second ROI 513 position may correspond to a position of the lesion in the comparative image. In some examples a lesion evaluation 514 may also be output by registration process 512. Lesion evaluation 514 may include prompts displayed to the user that the lesion is in or out of a desired region for the imaging process. In some examples, where the imaging process may be a biopsy, lesion evaluation 514 may include indicating by a prompt displayed to the user that lesion is in or out of a volume which may be accessed for biopsy. Further, registration process 512 may output repositioning instructions 516. Repositioning instructions 516 may be output as a prompt displayed to the user if the lesion is outside of an image frame. For example, repositioning instructions 516 may instruct a user to move a breast of a patient in a direction (e.g., left, right, up, or down) relative to an x-ray tube and detector.

Turning now to FIG. 6A-6B, annotated images 600 and 650 are shown. Annotated images 600 and 650 may be similar to annotated images output as a result of a registration process as described above with respect to FIG. 5 showing the relative position of a lesion. Annotated image 600 shown in FIG. 6A may include a scout image 602 wherein a lesion is within the image frame of the scout image (e.g., within a desired region). Scout image 602 may include an ROI 604 generated by the registration process which surrounds the lesion in scout image 602.

Annotated image 650 shown in FIG. 6B may include scout image 652 where a lesion is outside the image frame the scout image (e.g., outside of the desired region). As one example, annotated image 650 may include an arrow 654 pointing in a direction corresponding to where the lesion would be outside the frame of scout image 652. Additionally or alternatively, annotated image 650 may include bracket 656 which may indicate a one dimensional region (e.g., a length along an edge of scout image 652) in which the lesion may be located outside the frame of scout image 652. In other examples, annotated image 650 may additionally or alternatively include written (e.g., text), audio, or other symbolic instructions indicating where the lesion may be positioned relative scout image 652.

A scout image may be taken before an imaging procedure such as a CESM procedure. In one example, the CESM procedure may be performed as part of a biopsy procedure to increase a contrast of the lesion which is being biopsied. As described in FIG. 7 below, a registration process may be used to help identify a position of a lesion if visibility is lost during a CESM procedure due to x-ray scattering or contrast media being washed out of the lesion.

Turning now to FIG. 7, a method 700 is shown for using an image registration process (such a method 200 of FIG. 2) to determine a position of a lesion within an image frame during a CESM procedure. Method 700 may be executed using computer readable executable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 700 may be executed by another computing device without departing from the scope of this disclosure (e.g., an edge device, a picture archiving and communication system (PACS)). Outputs of method 700 may be visualized on a display connected in communication with the computing device.

At 702, method 700 includes acquiring a CESM image. A CESM image may be acquired after injection of a contrast medium such as iodine. Further, acquiring a CESM image may include acquiring both a high energy and low energy image and subtracting the two images to obtain a dual energy image as described above with respect to FIG. 1. The CESM image may be a scout image or an image acquired at any time during the CESM procedure.

At 704, method 700 includes determining if the lesion is visible in the CESM image. A CESM image with a visible lesion may be an image wherein the contrast medium is localized within the lesion and the lesion location may be confidently identified by the user or a CAD program. If the lesion is visible, method 700 continues to 716 and the CESM procedure proceeds. If the lesion is not visible in the CESM image, method 700 proceeds to 706 and includes selecting a reference image and a first ROI. Selecting the reference image and first ROI may be performed by a user. A lesion may not be visible in a CESM image if the contrast media has washed out of the lesion or if a biopsy needle is inserted and causes x-ray scattering. Additionally or alternatively, the lesion may not be visible in the CESM image because the patient has moved and the lesion is outside of a field of view of the CESM image. The reference image may be a previous CESM image taken at a beginning of the CESM procedure. The previous CESM image may be an HE, LE, or combined image as described above with respect to FIG. 1. At a beginning of the CESM procedure there may be less of a chance of washout or scattering obscuring the position of the lesion. Additionally or alternatively, the reference image may be a CESM image taken during a previous procedure, or an image taken using a different imaging modality such as MRI. The ROI may be designated by the user or automatically designated by CAD instructions stored on a controller which may be the same or different than the controller on which method 700 may be stored. In some examples, more the one reference image may be selected. For example, a CESM image from an earlier procedure and a non-CESM image from a previous exam may both be selected as reference images.

At 708, method 700 includes registering the reference image and the acquired CESM image. The registration process may map features of the selected reference image and ROI of step 706 onto features of the acquired CESM image. Registering the image may be include following steps of method 200 FIG. 2 and diagramed in FIG. 3 above.

As a result of step 708, method 700 includes indicating the position of the lesion with respect to the CESM image at 710. In one example, at 710, method 700 may include generating an annotated image including a second ROI surrounding the lesion. If the second ROI indicates that the lesion is no longer in a desired region of the CESM image at 710, method 700 may include at 712 indicating that the lesion is out of the desired region. The indication may be given as a first written text or symbolic notification appearing on the image. In an example where the CESM procedure is a biopsy procedure, method 700 may indicate with a second notification if the lesion is within a biopsy volume. In one example, the notification may include comparing the biopsy volume with the second ROI. Further, at 714, method 700 may include giving instructions to the user regarding a direction in which to reposition the patient so that the lesion may be in the desired region of the CESM image. As one example, directions may be indicated symbolically as described above with respect to FIG. 6B. Additionally or alternatively, directions may be given by written and/or audio prompts.

At 715, method 700 includes determining if the patient was repositioned. As described above, the patient may be repositioned based on the indicated position of the lesion at 710 to place the lesion within the desired region of the CESM image and/or within a biopsy volume. If the patient was repositioned, method 700 returns to 702. If the patient was not repositioned, method 700 proceeds to 716. The patient may not be repositioned if the lesion position is indicated at 710 and shows that the lesion is still in the desired region of the image and/or within the biopsy volume.

In this way, if the lesion position is not readily seen on the CESM image, a user may determine whether a position of the patient has changed, or if the lesion has lost contrast media, or both. When the user correctly determines the lesion position, a number of image retakes and thereby patient radiation exposure may be reduced. The CESM procedure may continue at 716 and a user may be able to identify a position of the lesion. Method 700 returns and may be repeated during a CESM procedure.

Figure 8:
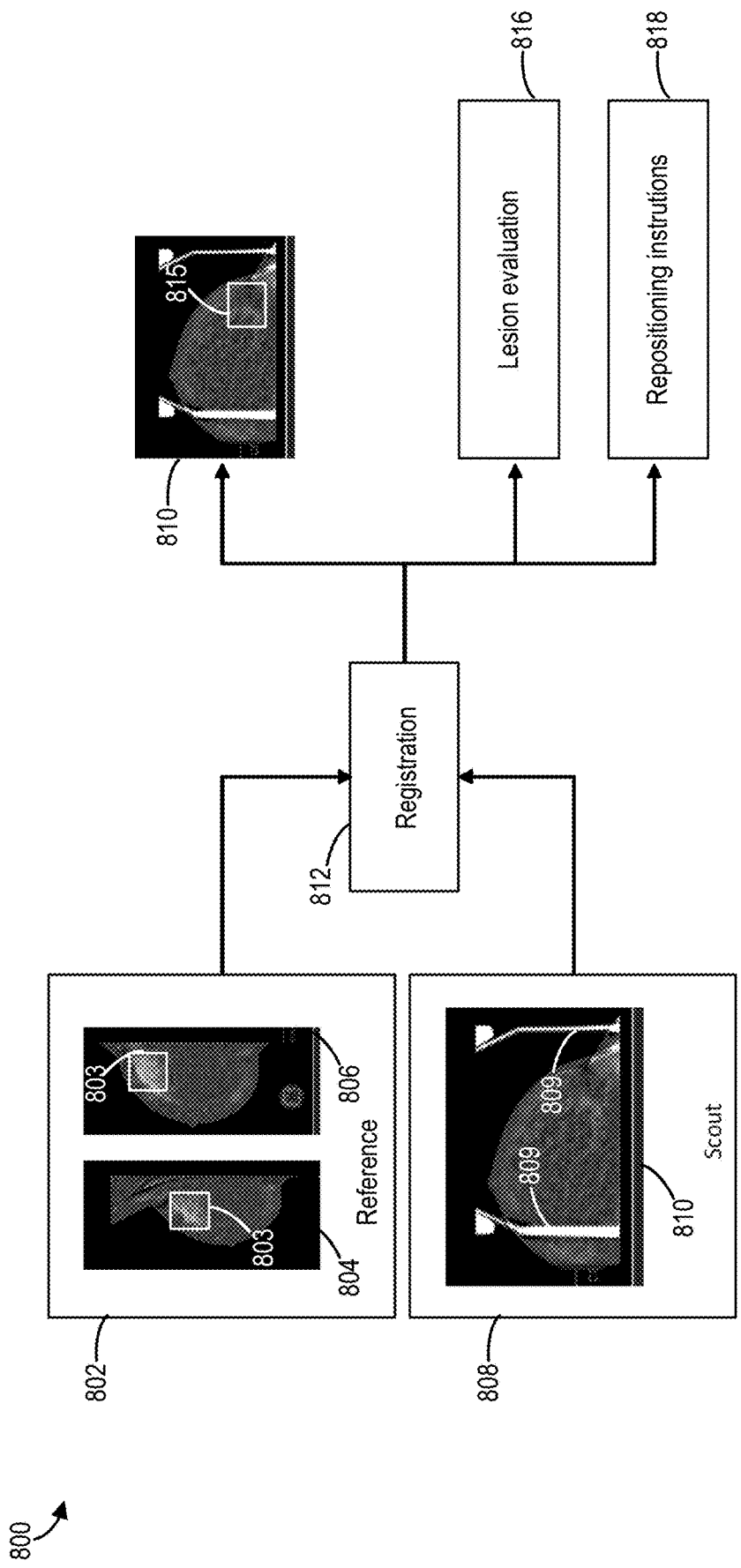
FIG. 8 schematically shows a process for identifying a position of a lesion during a CESM biopsy exam according to an embodiment.
Figure 9:
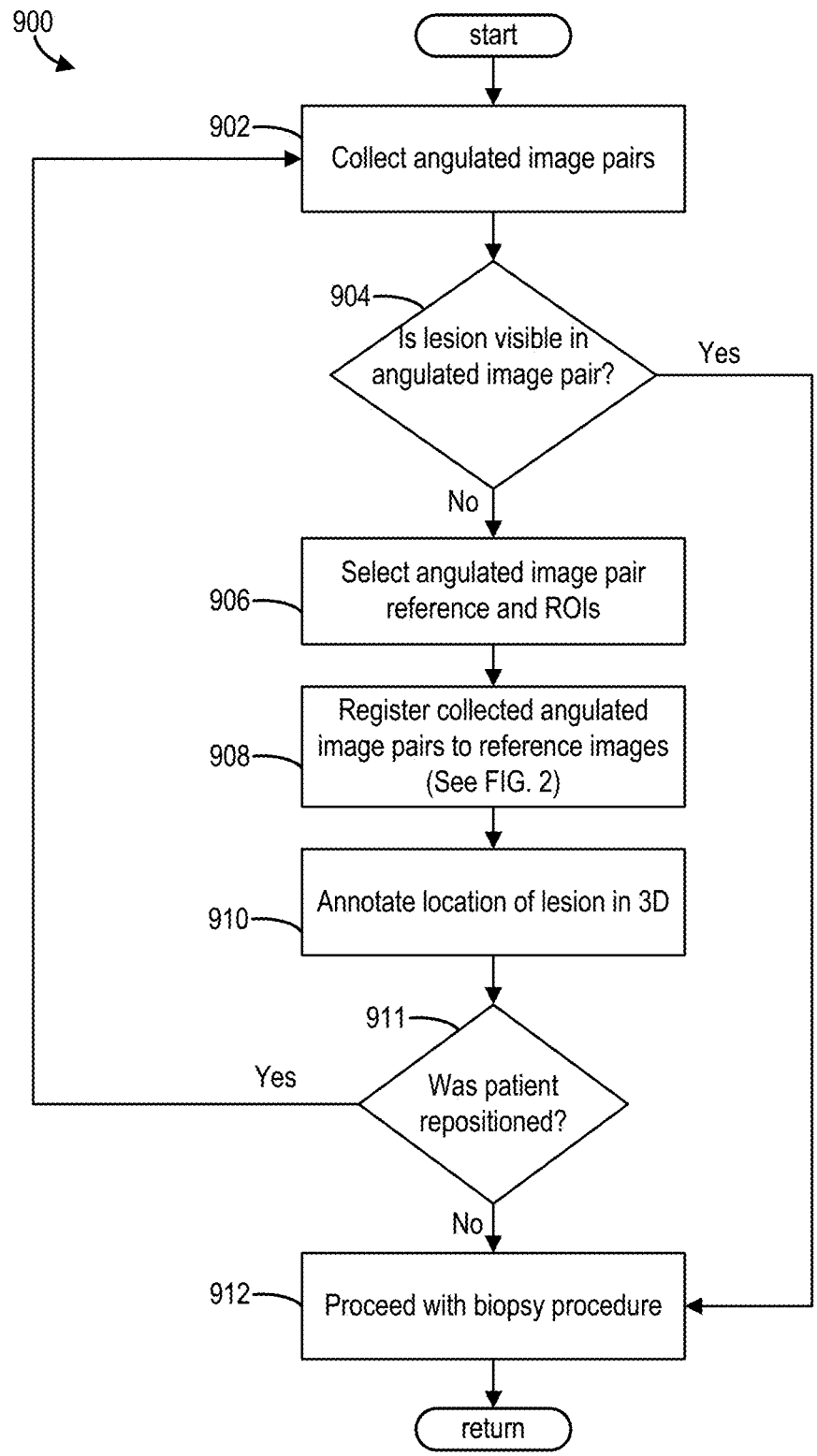
FIG. 9 shows a method for identifying a position of a lesion during a CESM stereotactic biopsy exam according to an embodiment.

Method 700 may be shown schematically via diagram 800 of FIG. 8. Diagram 800 may include reference images 802 and a comparison image 808. Reference images 802 may be CESM images where the lesion is visible. Reference images 802 may be HE, LE, or DE images or any combination thereof. Reference images may include an ROI 803 which may be placed by a user or by CAD program. Reference images 802 may include a first view 804 and a second 806. First view 804 and second view 806 may be different views of the same lesion wherein the lesion is readily identified. As described above with respect to method 700, reference images 802 may be collected during a beginning of a CESM procedure where interference due to washout of contrast media or scattering may be less likely.

Comparison image 808 may be an image 810 wherein the lesion is no longer identifiable. The lesion may no longer be identifiable due to x-ray scatter, washout of the CESM contrast media, or due to movement of the lesion outside of a field of view of the procedure. In one example, image 810 may be acquired at a different angle than first view 804 or second view 806. In some examples, image 810 may be a scout image. In other examples image 810 may be collected over the course of a CESM procedure which may be a biopsy procedure. Image 810 may also include artifacts 809, which may be present due to use of a compression paddle when the CESM procedure is a biopsy procedure.

Reference images 802 and comparison image 808 may be mapped onto each other via registration 812. Registration 812 may be similar to the registration process described above with respect to FIGS. 2 and 3. For example, a pre-registration process may define a region between artifacts 809 to register to the reference image.

Registration 812 may output image 810 with an annotation of ROI 815. ROI position 815 may correspond to a location of the lesion on comparison image 808. In some examples registration 812 may also output lesion evaluation 816. Lesion evaluation 816 may include communicating to the user if the lesion is in or out of the field of view. Further, lesion evaluation 816 may include communicating to the user if the lesion is in or out of a volume that may be accessed by a biopsy needle (e.g., biopsy volume). Communication of lesion evaluation 816 may include annotating comparison image 808 to indicate at which edge of comparison image 810 the lesion may be located, as described above with respect to FIG. 6B. The communication may also include other written or audio prompts to the user by the controller. In some examples registration 812 may also output repositioning instructions 818. Repositioning instructions 818 may be written or audio prompts to the user by the controller for moving a patient or components of a digital mammography system to move the lesion into the field of view.

As described above with respect to FIG. 1, a digital mammography system, such as digital mammography system 100, may be operated in tomosynthesis mode in which x-ray scans may be taken at different angles to assemble a stereotactic image which may be used to calculate positions in 3D. The different angled acquisitions (angulations) may be collected in pairs (e.g., +15° and −15°). In some examples, a position of a lesion may be easily identified in a first pair of angulations, but may become no longer visible during a subsequent acquisition. Additionally or alternatively, the digital mammography system may be operated in CE-DBT mode and a plurality of angulated images may be collected to form a 3D image, as described above with respect to FIG. 1. An image registration process as described below with respect to FIG. 9 may be able to locate the position of the lesion in any 3D position.

Turning now to FIG. 9, a method 900 is shown for using an image registration process (such a method 200 of FIG. 2) to determine a position of a lesion relative to a field of view of an image during a biopsy procedure. Method 900 may be executed using computer readable executable instructions stored in the non-transitory memory of a computing device of a digital mammography system (e.g., digital mammography system 100 of FIG. 1) or a controller communicatively coupled to the digital mammography system (e.g., controller 44 of FIG. 1). In some embodiments, method 900 may be executed by another computing device without departing from the scope of this disclosure (e.g., an edge device, a picture archiving and communication system (PACS)). Outputs of method 900 may be visualized on a display connected in communication with the computing device.

At 902, method 900 includes collecting angulated pairs of x-ray images. The angulated x-ray image pairs may be collected at displacement angles of the x-rays (e.g., +15° and −15°). In some examples, the angulated pairs of images may be CESM images whereby a LE, and HE images may be collected. In an alternate example, a plurality of angulated images may be collected as part of a CE-DBT procedure.

At 904, method 900 includes determining if the lesion is visible in the angulated x-ray images. In some examples where a contrast media is used, the lesion visibility may depend on whether the contrast media has washed out of lesion area. In other examples, the angulated pair of images may be taken with a biopsy needle inserted into the breast tissue, whereby the biopsy needle may obscure the position of the lesion. If the lesion is visible, method 900 proceeds to 912 and includes continuing the biopsy procedure.

If the lesion is not visible, method 900 includes, at 906, selecting a pair of angulated images as reference images and first ROIs. The first ROIs may be added by a user or CAD program to identify a location of the lesion. In an example where CESM images are collected, the reference images may be collected at a beginning of the procedure, before the contrast media is washed out from the lesion area. Further, the pair of angulated images selected as reference images may be HE, LE, or DE images. In some examples, a scout image taken at the beginning of the procedure may also be selected as a reference image. In other examples, the pair of angulated images may be taken during a previous imaging session. Additionally or alternatively, reference images may be selected from a CE-DBT procedure and may include a plurality of angulated images. Further, more than one set of reference images may be chosen.

At 908, method 900 includes registering the collected angulated pair where the lesion is not visible to the reference image as selected at 906. Image registration may be performed following the method described above with respect to FIGS. 2 and 3.

At 910, method 900 includes annotating the location of the lesion in the 2D stereotactic image on which registration was performed. In an example where CESM images are collected, the location may be annotated in HE, LE or DE images. The annotations may include indicating a position of the lesion on the stereotactic 2D images, from which the 3D position of the lesion may be calculated and of a second set of ROIs may be generated around the lesion. In an example where the reference images are of a DBT procedure, the second set of ROIs may be generated on a 3D image. Further, whether or not the lesion is within a target biopsy volume may be addressed by a notification shown on a display of the computing unit. Additionally or alternatively, annotations may indicate if the lesion is not within a field of view of the image and may give indications of a direction of the lesion relative to the image.

At 911, method 900 determines if the patient was repositioned. The patient may be repositioned to place the lesion within the target biopsy volume and/or the field of view of the stereotactic images. If the patient was repositioned, method 900 returns to 902. If the patient was not repositioned, method 900 proceeds to 912. The patient may not be repositioned if at 910 the annotated image shows the lesion is in the frame of the stereotactic images and within the target biopsy region. At 912, a biopsy procedure is performed. The biopsy procedure may continue to collect images of the lesion at different angulated image pairs. Method 900 returns.

Figure 10:
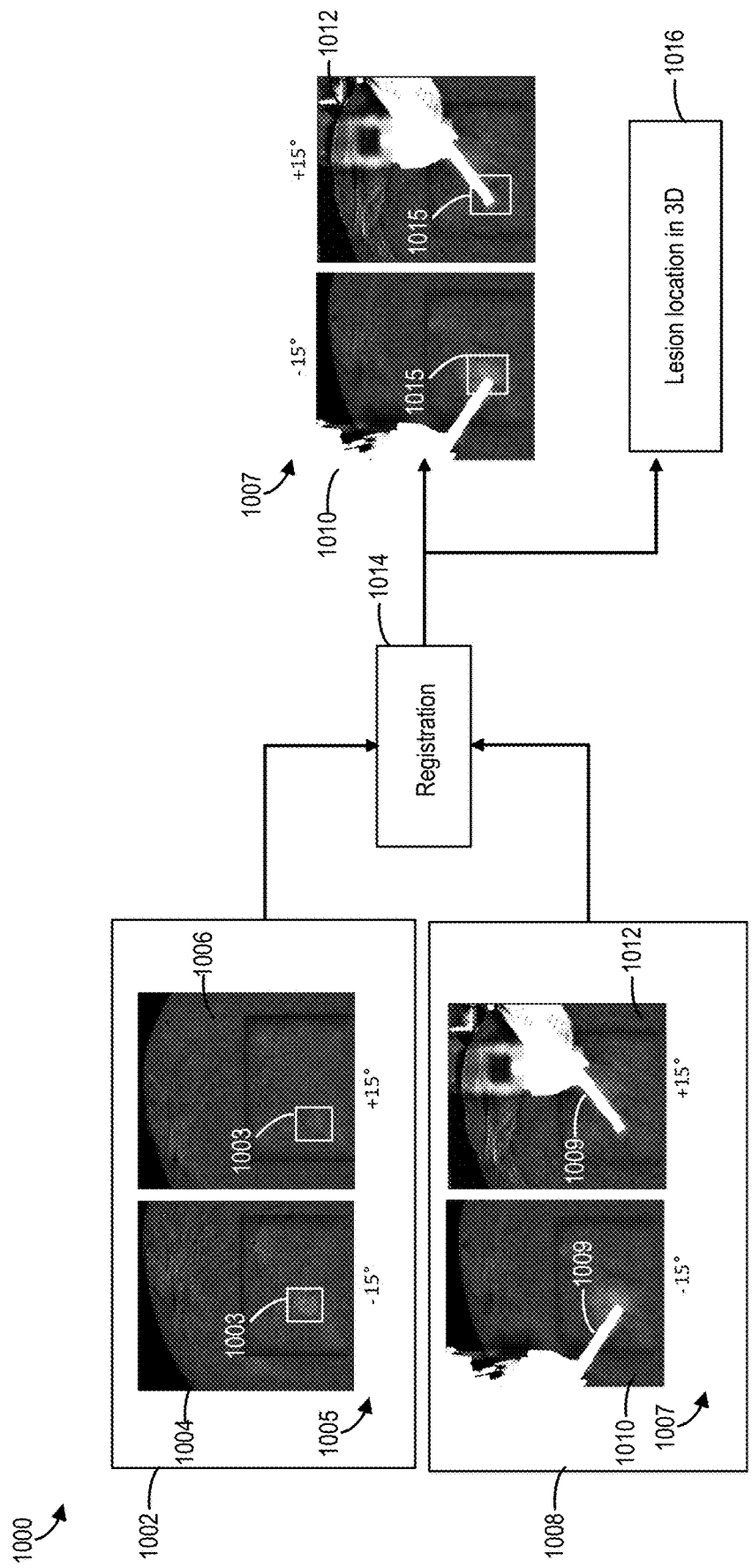
FIG. 10 schematically shows identifying a position of a lesion during a CESM stereotactic biopsy exam according to an embodiment.

Method 900 may be shown schematically by diagram 1000 of FIG. 10. Diagram 1000 includes reference images 1002 and comparison images 1008. Reference images 1002 may include a first reference angulated image 1004 and a second reference angulated image 1006. First reference angulated image 1004 and second reference angulated image 1006 may together comprise an angulated image pair 1005. Angulated image pair 1005 may be taken at equal and opposite rotations of an x-ray system, such as x-ray system 10 of FIG. 1. First reference angulated image 1004 and second reference angulated image 1006 may each include an ROI 1003 identifying a location of the lesion. ROI 1003 may be placed by a user or by a CAD program.

Comparison images 1008 may include a first comparison angulated image 1010 and a second comparison angulated image 1012 which together may comprise an angulated image pair 1007. Angulated image pair 1007 may be collected at the same or different pair of angles as angulated image pair 1005. The position of the lesion may no longer be visible in angulated image pair 1007. As shown in FIG. 10, the lesion may no longer visible due to obstruction by a biopsy needle 1009. In other examples the lesion may no longer be visible due to a contrast media becoming washed out or due to scatter or the x-rays.

Reference images 1002 and comparison images 1008 may be inputs to registration process 1014. Registration process 1014 may map features of reference images 1002 onto comparison images 1008 according to the method described above with respect to FIGS. 2 and 3.

Registration process 1014 may output angulated image pair 1007 including ROI 1003 annotating the location of the lesion in first comparison angulated image 1010 and in second comparison angulated image 1012. Further, registration process 1014 may output a location of the lesion 1015 on comparison images 1008. The location of the lesion in 3D 1016 may include the location of the lesion across any angulated image taken during the procedure.

The technical effect of methods 400 of FIG. 4, 700 of FIG. 7, and 900 of FIG. 9 is to allow a user to identify, with increased certainty and efficiency, a position of a lesion relative to a digital mammography image using a previous identified position in a different image. The methods may allow the user to differentiate between a lesion present in an image but not visible and a lesion not present in an image due to patient positioning. A reference image used for methods described above may be an earlier digital mammography image taken during a current or previous imaging procedure or an image taken using a different imaging modality. In this way, a user may more readily identify a lesion within an image or be instructed to move a patient in a direction to place the lesion within a frame of the image. A time and radiation dose required for the procedure may be minimized due to increased speed and accuracy in identifying the position of the lesion.

The disclosure also provides support for a method for imaging, comprising: acquiring a comparative image of a patient, aligning the comparative image with a reference image, at a processor, by registering the comparative image to the reference image, the reference image including an ROI corresponding to a lesion, mapping the ROI of the reference image onto the comparative image, and displaying the comparative image at a display screen with instructions indicating a relative position of the ROI in response to the ROI being outside of a desired region of the comparative image. In a first example of the method, the comparative image is a scout image acquired with an x-ray detector. In a second example of the method, optionally including the first example, the reference image is one or more of an x-ray image, ultrasound (US) image, or magnetic resonance imaging (MRI) image, the ROI of the reference image being outside of the desired region of the comparative image. In a third example of the method, optionally including one or both of the first and second examples, the reference image is taken prior to the comparative image during one of a separate imaging procedure or a same imaging procedure as the comparative image. In a fourth example of the method, optionally including one or more or each of the first through third examples, the reference image is a scout image acquired with an x-ray detector and the comparative image is taken prior to the reference image during one of a separate imaging procedure or a same imaging procedure. In a fifth example of the method, optionally including one or more or each of the first through fourth examples, registering the comparative image includes pre-processing the comparative image to define a region free from artifacts in the comparative image. In a sixth example of the method, optionally including one or more or each of the first through fifth examples, the method further comprises: comparing the ROI position to a biopsy volume indicated on a display of a workstation, and, in response to the ROI being outside of the biopsy volume, instructions for repositioning the patient are displayed. In a seventh example of the method, optionally including one or more or each of the first through sixth examples, displaying the comparative image at the display screen with the instructions includes displaying one or more of text indicating how to reposition the patient, text indicating a location of the lesion relative to the desired region of the comparative image, and arrows indicating the location of the lesion relative to the desired region of the comparative image.

The disclosure also provides support for a system for digital mammography, comprising: an x-ray source in communication with a detector, a display device, and a computing device connected in communication with the display device and with the detector, the computing device including a processor and non-transitory memory storing instructions executable by the processor to: acquire a scout image of a breast, register, with the processor, the scout image to a reference image, the reference image including a first ROI identifying a position of a lesion in the reference image and collected before acquiring the scout image, generate, in response to the lesion being within a frame of the scout image and with the processor, a second ROI on the scout image identifying the position of the lesion in the scout image and indicate if the position of the lesion is within a biopsy volume, and display, in response to the lesion being outside of the frame of the scout image, a first notification on a display screen. In a first example of the system, the scout image and reference image form a pair of angulated x-ray images or the scout and reference image are contrast enhanced spectral mammography (CESM) images. In a second example of the system, optionally including the first example, the reference image is an x-ray image, an ultrasound (US) image, or a magnetic resonance imaging (MRI) image. In a third example of the system, optionally including one or both of the first and second examples, the first ROI of the reference image is placed by a clinician or computer aided diagnosis (CAD) program. In a fourth example of the system, optionally including one or more or each of the first through third examples, instructions to indicate if the position of the lesion within the biopsy volume include to display a second notification on the display screen and/or to generate an audio notification. In a fifth example of the system, optionally including one or more or each of the first through fourth examples, the first or second notifications include written instructions or symbolic instructions.

The disclosure also provides support for a system for digital mammography, comprising: an x-ray source in communication with a detector, a display device, and a computing device connected in communication with the display device and with the detector, the computing device including a processor and non-transitory memory storing instructions executable by the processor to: register one or more reference images including a first ROI to a comparative image, the first ROI indicating a position of a lesion on the one or more reference images, and indicate a position of the lesion with respect to the comparative image. In a first example of the system when the position of the lesion is within a frame of the comparative image, the position is indicated as a second ROI on the comparative image. In a second example of the system, optionally including the first example when the position of the lesion is outside the frame of the comparative image, the position is indicated as directions displayed at the display device to reposition a patient. In a third example of the system, optionally including one or both of the first and second examples, the one or more reference images and comparative image are taken using common or different imaging modalities. In a fourth example of the system, optionally including one or more or each of the first through third examples, the one or more reference images are CESM images. In a fifth example of the system, optionally including one or more or each of the first through fourth examples, the comparative image is a CESM image taken after contrast agent washout.

FIG. 1 shows an example configuration with relative positioning of various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being coupling, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for imaging, comprising:
   acquiring a comparative image of a patient;
   aligning the comparative image with a reference image, at a processor, by registering the comparative image to the reference image, the reference image including an ROI corresponding to a lesion;
   mapping the ROI of the reference image onto the comparative image; and
   displaying the comparative image at a display screen with instructions indicating a relative position of the ROI in response to the ROI being outside of a desired region of the comparative image.

2. The method of claim 1, wherein the comparative image is a scout image acquired with an x-ray detector.

3. The method of claim 1, wherein the reference image is one or more of an x-ray image, ultrasound (US) image, or magnetic resonance imaging (MRI) image, the ROI of the reference image being outside of the desired region of the comparative image.

4. The method of claim 1, wherein the reference image is taken prior to the comparative image during one of a separate imaging procedure or a same imaging procedure as the comparative image.

5. The method of claim 1, wherein the reference image is a scout image acquired with an x-ray detector and the comparative image is taken prior to the reference image during one of a separate imaging procedure or a same imaging procedure.

6. The method of claim 1, wherein registering the comparative image includes pre-processing the comparative image to define a region free from artifacts in the comparative image.

7. The method of claim 1, further comprising comparing the ROI position to a biopsy volume indicated on a display of a workstation, and, in response to the ROI being outside of the biopsy volume, instructions for repositioning the patient are displayed.

8. The method of claim 1, wherein displaying the comparative image at the display screen with the instructions includes displaying one or more of text indicating how to reposition the patient, text indicating a location of the lesion relative to the desired region of the comparative image, and arrows indicating the location of the lesion relative to the desired region of the comparative image.

9. A system for digital mammography, comprising: an x-ray source in communication with a detector; a display screen; and a computing device connected in communication with the display screen and with the detector, the computing device including a processor and non-transitory memory storing instructions executable by the processor to: acquire a scout image of a breast; register, with the processor, the scout image to a reference image, the reference image including a first ROI identifying a position of a lesion in the reference image and collected before acquiring the scout image; generate, in response to the lesion being within a frame of the scout image and with the processor, a second ROI on the scout image identifying the position of the lesion in the scout image and indicate if the position of the lesion is within a biopsy volume; and display, in response to the lesion being outside of the frame of the scout image, a first notification on the display screen.

10. The system of claim 9, wherein the scout image and reference image form a pair of angulated x-ray images or the scout and reference image are contrast enhanced spectral mammography (CESM) images.

11. The system of claim 9, wherein the reference image is an x-ray image, an ultrasound (US) image, or a magnetic resonance imaging (MRI) image.

12. The system of claim 9, wherein the first ROI of the reference image is placed by a clinician or computer aided diagnosis (CAD) program.

13. The system of claim 9, wherein instructions to indicate if the position of the lesion within the biopsy volume include to display a second notification on the display screen and/or to generate an audio notification.

14. The system of claim 9, wherein the first or second notifications include written instructions or symbolic instructions.

15. A system for digital mammography, comprising:
an x-ray source in communication with a detector;
a display device; and
a computing device connected in communication with the display device and with the detector, the computing device including a processor and non-transitory memory storing instructions executable by the processor to:
register one or more reference images including a first ROI to a comparative image, the first ROI indicating a position of a lesion on the one or more reference images; and
indicate a position of the lesion with respect to the comparative image.

16. The system of claim 15, wherein, when the position of the lesion is within a frame of the comparative image, the position is indicated as a second ROI on the comparative image.

17. The system of claim 16, wherein, when the position of the lesion is outside the frame of the comparative image, the position is indicated as directions displayed at the display device to reposition a patient.

18. The system of claim 15, wherein the one or more reference images and comparative image are taken using common or different imaging modalities.

19. The system of claim 15, wherein the one or more reference images are CESM images.

20. The system of claim 15, wherein the comparative image is a CESM image taken after contrast agent washout.

* * * * *